(12) United States Patent
Starch et al.

(10) Patent No.: US 9,173,832 B2
(45) Date of Patent: Nov. 3, 2015

(54) PITUITOUS SILICONE FLUIDS

(71) Applicant: Dow Corning Corporation, Midland, MI (US)

(72) Inventors: Michael Stephen Starch, Midland, MI (US); Paul Cornelius Vandort, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/279,693

(22) Filed: May 16, 2014

(65) Prior Publication Data
US 2014/0249106 A1    Sep. 4, 2014

Related U.S. Application Data

(62) Division of application No. 13/392,580, filed as application No. PCT/US2010/047479 on Sep. 1, 2011, now abandoned.

(60) Provisional application No. 61/239,529, filed on Sep. 3, 2009, provisional application No. 61/239,533, filed on Sep. 3, 2009.

(51) Int. Cl.
| | |
|---|---|
| *A61K 8/891* | (2006.01) |
| *A61K 8/895* | (2006.01) |
| *A61Q 19/00* | (2006.01) |
| *C08G 77/50* | (2006.01) |
| *C08L 83/14* | (2006.01) |

(52) U.S. Cl.
CPC ............... *A61K 8/891* (2013.01); *A61K 8/895* (2013.01); *A61Q 19/00* (2013.01); *C08G 77/50* (2013.01); *C08L 83/14* (2013.01)

(58) Field of Classification Search
None
See application file for complete search history.

(56) References Cited

U.S. PATENT DOCUMENTS

| | | |
|---|---|---|
| 6,291,563 B1 * | 9/2001 | Horne et al. .................. 524/267 |
| 2004/0138376 A1 | 7/2004 | Awad |
| 2004/0236054 A1 | 11/2004 | George et al. |
| 2006/0116500 A1 | 6/2006 | Chapman et al. |
| 2008/0058491 A1 | 3/2008 | Schlitzer et al. |
| 2010/0303743 A1 | 12/2010 | Garaud et al. |

FOREIGN PATENT DOCUMENTS

| | | |
|---|---|---|
| EP | 0922734 | 6/1999 |
| EP | 1057476 | 3/2003 |
| WO | 2006004518 | 5/2006 |

* cited by examiner

*Primary Examiner* — Michael B Pallay
(74) *Attorney, Agent, or Firm* — Baltazar Gomez

(57) ABSTRACT

Fluid compositions are disclosed containing a branched organopolysiloxane and a carrier fluid. The branched organopolysiloxane is obtainable by reacting an organohydrogencyclosiloxane and an alkenyl terminated polydiorganosiloxane. The disclosed fluid compositions possess pituitous rheological properties.

5 Claims, 2 Drawing Sheets

FIG. 1 Normal Force Measurements for Branched silicone fluids as detailed in Example 1

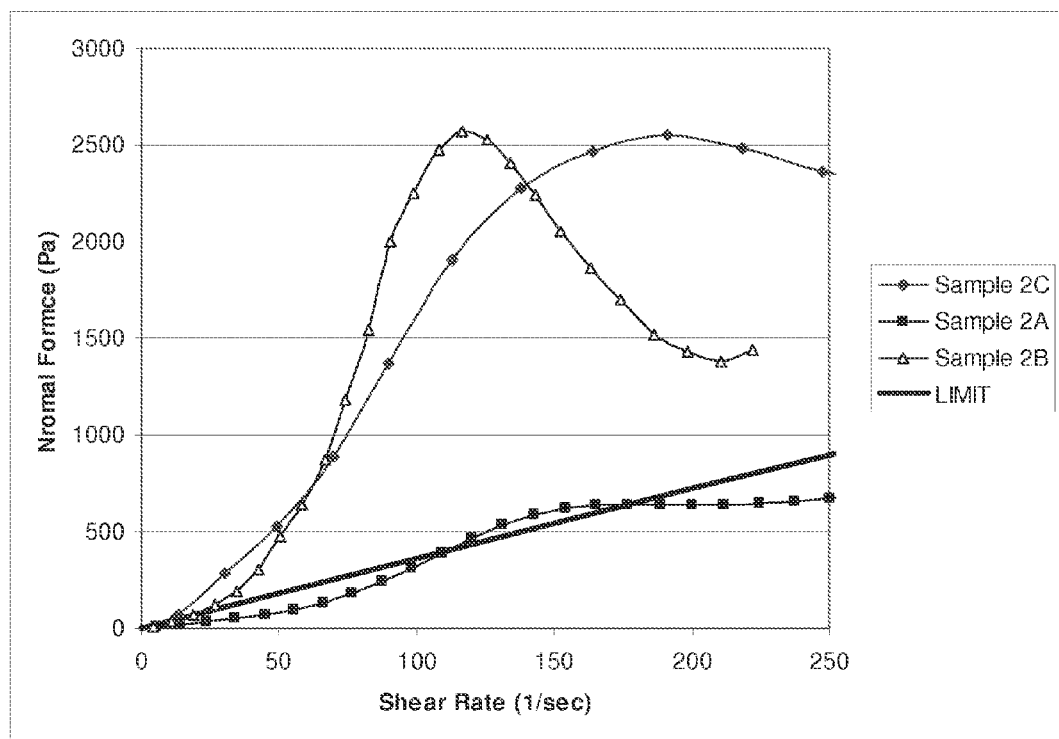
FIG. 2 Normal Force Measurements for Branched silicone fluids as detailed in Example 2

PITUITOUS SILICONE FLUIDS

CROSS REFERENCE TO RELATED APPLICATIONS

This is a divisional application of U.S. application Ser. No. 13/392,580 which was a U.S. national stage filing under 35 U.S.C. §371 of PCT Application No. PCT/US10/47479 filed on Sep. 1, 2010 claiming the benefit of U.S. Provisional Patent Application No. 61/239,529 filed Sep. 3, 2009 and U.S. Provisional Patent Application No. 61/239,533 filed Sep. 3, 2009 under 35 U.S.C. §119 (e).

TECHNICAL FIELD

This disclosure relates to fluid compositions containing a branched organopolysiloxane and a carrier fluid. The branched organopolysiloxane is obtainable by reacting an organohydrogencyclosiloxane and an alkenyl terminated polydiorganosiloxane. The disclosed fluid compositions possess pituitous rheological properties.

BACKGROUND

Besides providing certain functional benefits, silicones are incorporated into personal care products for their inherent aesthetic benefits. In particular, formulators will optimize the overall aesthetics of personal care products by selecting certain types and amounts of a silicone. As such, there is a continuing need in this industry to discover new silicone compositions that provide improved product aesthetics, sensory perceptions, or functional improvements. The present inventors have discovered certain silicone fluid compositions that provide such improvements.

SUMMARY

This disclosure relates to a fluid composition comprising:
A) 0.1 to 50 wt % of a branched organopolysiloxane prepared by reacting;
  a) an organohydrogencyclosiloxane having the formula $[(CH_3)HSiO]_g$ where g is 3 to 8, and,
  b) an alkenyl terminated polydiorganosiloxane comprising siloxy units of the formula $(R_2R^2SiO_{1/2})_v(R_2SiO_{2/2})_x$ where v≥2, and x≥50,
    R is an alkyl group containing 1 to 6 carbon atoms,
    $R^2$ is an alkenyl group containing 2 to 12 carbon atoms,
  in the presence of a hydrosilylation catalyst, where the molar ratio of alkenyl groups to SiH in the reaction is between 0.9/1 to 2.2/1, and
B) 50 to 99.9 wt % of a carrier fluid,
wherein the fluid composition has a viscosity of at least 100 mPa·s (cP) at 23° C. and exhibits pituitous rheological properties.

Pituitous fluids are fluids that display particular types of rheological behavior. The most easily recognized rheological behavior for the pituitous fluids is their "stringing" behavior, which is the formation of thin strings or threads when a small amount of the pituitous fluid is separated from the bulk of the fluid. Another rheological characteristic exhibited by pituitous fluids is that they develop a normal force when subjected to shear stress. When a pituitous fluid is subjected to shear stress in the x-y plane, a force is developed in the z direction (perpendicular, or "normal" to the plane of shear). This behavior is related to a phenomenon known as the Weissenberg Effect whereby polymers in solution that are stirred tend to climb up the stirrer due to entanglements between polymer chains that develop under shear stress. Using a controlled stress rheometer, the normal force may be measured.

The pituitous silicone fluids of this disclosure are often highly lubricious yet form very persistent films on surfaces. As the pituitous fluids are sheared, the normal force developed resists thinning of the fluid and thereby maintaining a thicker lubrication layer between the moving surfaces. We have found that that certain branched and high molecular weight silicone fluids exhibit novel sensory and film-forming properties and these properties correlate with pituitous rheological behavior.

DETAILED DESCRIPTION

Figure 1:
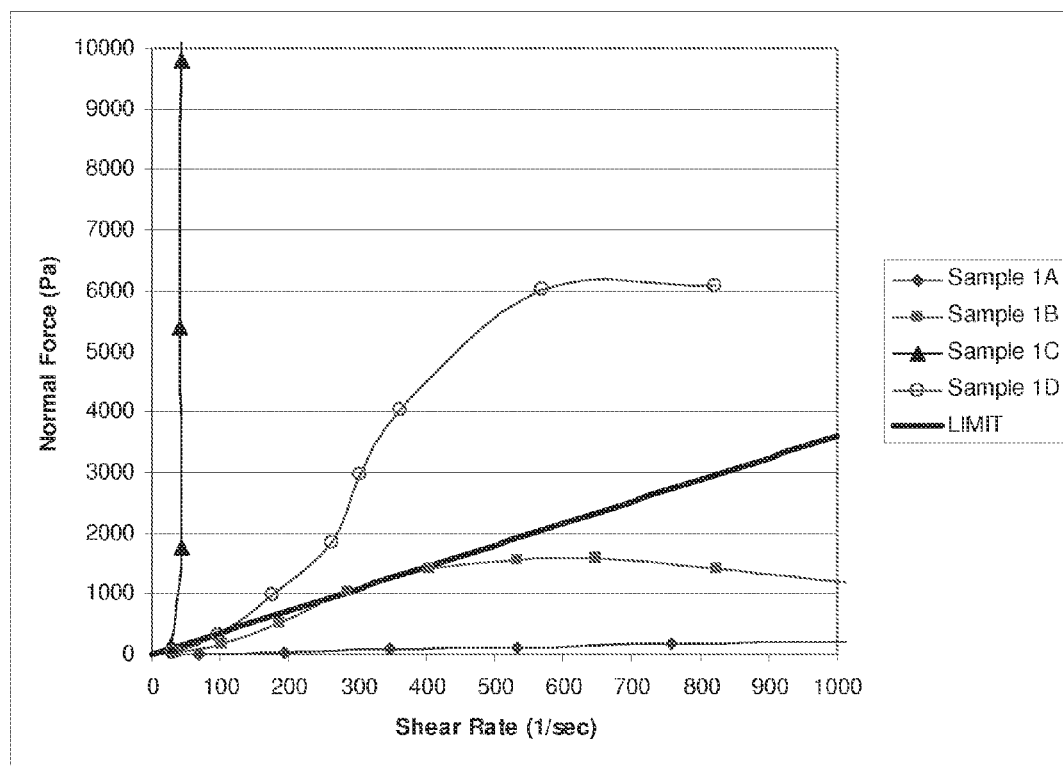
FIG. 1—Normal Force Measurements for Branched silicone fluids as detailed in Example 1
FIG. 2—Normal Force Measurements for Branched silicone fluids as detailed in Example 2

This disclosure relates to a fluid composition comprising:
A) 0.1 to 50 wt % of a branched organopolysiloxane prepared by reacting;
  a) an organohydrogencyclosiloxane having the formula $[(CH_3)HSiO]_g$ where g is 3 to 8, and,
  b) an alkenyl terminated polydiorganosiloxane comprising siloxy units of the formula $(R_2R^2SiO_{1/2})_v(R_2SiO_{2/2})_x$ where v≥2, and x≥50,
    R is an alkyl group containing 1 to 6 carbon atoms,
    $R^2$ is an alkenyl group containing 2 to 12 carbon atoms,
  in the presence of a hydrosilylation catalyst, where the molar ratio of alkenyl groups to SiH in the reaction is between 0.9/1 to 2.2/1, and
B) 50 to 99.9 wt % of a carrier fluid,
wherein the fluid composition has a viscosity of at least 100 mPa·s (cP) at 23° C. and exhibits pituitous rheological properties.

As used herein "fluid" means a liquid whose component particles can move past one another, that is flow, when a force is applied such as gravity. As used herein, "fluids" do not encompass "gels", which do not flow.

The fluid compositions of the present invention have a viscosity of at least 100 mPa·s (cP) at 23° C., alternatively of at least 200 mPa·s (cP) at 23° C., or alternatively 300 mPa·s (cP) at 23° C.

This disclosure provides certain silicone fluid compositions having pituitous rheological properties. As used herein, "pituitous" refers to the rheological property of an increasing normal force (typically measured in Pascals) observed in the perpendicular direction when a constantly increasing shear (typically measured in $sec^{-1}$) is applied to a film or layer of the fluid. In other words, when a pituitous fluid is subjected to shear stress in the x-y plane, a force is developed in the z direction (perpendicular or normal to the plane of shear). Pituitous rheology of the present silicone fluids may be measured using a controlled stress rheometer. Such rheometers are commercially available, such as TA Instruments AR 1000-N (109 Lukens Drive, New Castle Del. 19720). The fluid is held between a flat disk (attached to the rheometer) and a stationary plate equipped with a load cell. A controlled amount of force (torque) is applied to the shaft attached to the disc thus subjecting the sample to a shear stress. Typically, the torque is increased during the experiment and the disc rotates at an increasing rate which is recorded as the shear rate. As the fluid sample is being subjected to the shear stress, the normal force is recorded by the load cell. The results of the evaluations of the silicone fluid rheological properties using such instruments are reported as a plot of normal force in Pascals vs a perpendicular shear rate in sec$^{-1}$.

The fluid compositions of the present disclosure possess rheological properties such that when a plot of normal force in Pascal vs a perpendicular shear rate in sec$^{-1}$ is measured using a controlled stress rheometer as described above, the plot has an average slope that is greater than 3.6.

A) The Branched Organopolysiloxane

The branched organopolysiloxane is obtainable by reacting;
a) an organohydrogencyclosiloxane having the formula [(CH$_3$)HSiO]$_g$ where g is 3 to 8 and,
b) an alkenyl terminated polydiorganosiloxane comprising siloxy units of the formula (R$_2$R$^2$SiO$_{1/2}$)$_v$(R$_2$SiO$_{2/2}$)$_x$ where v≥2, and x≥50,
R is an alkyl group containing 1 to 6 carbon atoms,
R$^2$ is an alkenyl group containing 2 to 12 carbon atoms,
in the presence of a hydrosilylation catalyst, where the molar ratio of alkenyl groups to SiH in the reaction is between 0.9/1 to 2.2/1.

The organohydrogencyclosiloxanes useful as component a) have the formula [(CH$_3$)HSiO]$_g$ where g is 3 to 8, or mixtures thereof. Alternatively organohydrogencyclosiloxanes may be selected where g is 4 to 6, or alternatively g is 4.

Component b) is an alkenyl terminated polydiorganosiloxane. Component b) may be selected from any organopolysiloxane, or mixture of organopolysiloxanes comprising siloxy units represented by the formula (R$_2$R$^2$SiO$_{1/2}$)$_v$(R$_2$SiO$_{2/2}$)$_x$ where v≥2, and x≥50, alternatively x≥100, R is a hydrocarbon or halogen substituted hydrocarbon containing 1 to 20 carbons, alternatively an alkyl group containing 1 to 12 carbons, alternatively an alkyl group containing 1 to 6 carbons or alternatively methyl. The monovalent hydrocarbon group R having from 1 to 20 carbon atoms is exemplified by alkyl groups such as: methyl, ethyl, propyl, butyl, hexyl, octyl, and decyl; cycloaliphatic groups such as cyclohexyl; aryl groups such as phenyl, tolyl, and xylyl, and aralkyl groups such as benzyl and phenylethyl. R$^2$ is an alkenyl group containing 2 to 12 carbon atoms. The R$^2$ alkenyl groups of component b) are exemplified by vinyl, allyl, 3-butenyl, 4-pentenyl, 5-hexenyl, 6-heptenyl, 7-octenyl, 8-nonenyl, 9-decenyl, 10-undecenyl, 4,7-octadienyl, 5,8-nonadienyl, 5,9-decadienyl, 6,11-dodecadienyl and 4,8-nonadienyl.

The polydiorganosiloxane can be a homopolymer, a copolymer or a terpolymer containing such organic groups. Examples include copolymers comprising dimethylsiloxy units and phenylmethylsiloxy units, copolymers comprising dimethylsiloxy units and 3,3,3-trifluoropropylmethylsiloxy units, copolymers of dimethylsiloxy units and diphenylsiloxy units and interpolymers of dimethylsiloxy units, diphenylsiloxy units and phenylmethylsiloxy units, among others. The molecular structure is also not critical and is exemplified by straight-chain and partially branched straight-chain structures, the linear systems being the most typical.

The alkenyl terminated polydiorganosiloxane may also contain other siloxy units, such as "T" units (RSiO$_{3/2}$) and "Q" siloxy units (SiO$_{4/2}$).

Component b) may also be a mixture of any of the aforementioned organopolysiloxanes. The molecular weights, or the degree of polymerization (as designated by subscript (x) may vary providing x is greater than or equal to 50, otherwise the molecular weights are not limiting. However, when molecular weights become too high or if the organopolysiloxane is a solid, it may be desirable to dilute component b) in a suitable solvent or lower molecular weight fluid, such as any of the carrier fluids described below.

Component b) may be selected from vinyl functional endblocked polydimethylsiloxanes (vinyl siloxanes) or hexenyl functional endblocked polydimethylsiloxanes (hexenyl siloxanes), such as those having the average formula;

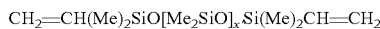

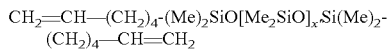

wherein Me is methyl,
x'≥50.

Vinyl or hexenyl functional polydimethylsiloxanes are known, and there are many commercially available. Representative, non-limiting examples include DOW CORNING® fluids; SFD 128, DC4-2764, DC2-7891, DC2-7754, DC2-7891, and DC 2-7463, SFD-117, SFD-119, SFD 120, SFD 129, DC 5-8709, LV, 2-7038, DC 2-7892, 2-7287, 2-7463, and dihexenyl terminal DC7692, DC7697 (Dow Corning Corporation, Midland, Mich.).

In one embodiment, the alkenyl terminated polydiorganosiloxane is selected from a polydiorganosiloxane gum. As used herein, polydiorganosiloxane gums are organopolysiloxanes comprising predominately D siloxy units and are of sufficient molecular weight to impart pituitous behavior to the silicone fluid compositions. Alternatively, the polydiorganosiloxane gum is of sufficient molecular weight to impart a viscosity of at least 1,000,000 mm$^2$/s at 25° C., or alternatively 2,000,000 mm$^2$/s at 25° C. Alternatively, the molecular weight of the diorganopolysiloxane gum is sufficient to impart a Williams plasticity number of at least 40 as determined by the American Society for Testing and Materials (ASTM) test method 926. Typically, the plasticity number should be 40 to 200, or alternatively 50 to 150. Alternatively, the molecular weight of the diorganopolysiloxane gum is at least 600,000 Daltons, or alternatively at least 1,000,000 Daltons, or alternatively at least 2,000,000 Daltons.

The silicon-bonded organic groups of the diorganopolysiloxane may be independently selected from hydrocarbon, or halogenated hydrocarbon groups. The hydrocarbon groups may be specifically exemplified by alkyl groups having 1 to 20 carbon atoms, such as methyl, ethyl, propyl, butyl, pentyl and hexyl; cycloalkyl groups, such as cyclohexyl and cycloheptyl; aryl groups having 6 to 12 carbon atoms, such as phenyl, tolyl and xylyl; aralkyl groups having 7 to 20 carbon atoms, such as benzyl and phenylethyl. The hydrocarbon group may also be an alkenyl group having 2 to 20 carbon atoms exemplified by vinyl, allyl, butenyl, pentenyl, hexenyl and decenyl, preferably vinyl or hexenyl groups. The halogenated alkyl groups may have 1 to 20 carbon atoms, such as 3,3,3-trifluoropropyl and chloromethyl.

Specific illustrations of diorganopolysiloxane gums include: dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; dimethylvinylsiloxy-endblocked methylphenylsiloxane-dimethylsiloxane-methylvinylsiloxane copolymers; and similar copolymers wherein at least one end group contains a vinyl group.

Methods for preparing diorganopolysiloxane gums are well known and many are commercially available. Representative commercial products suitable in the present silicone compositions include; Dow Corning® SGM-36 Gum and SGM-3 Gum.

The reaction between components a) and b) is conducted in the presence of a hydrosilylation catalyst. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as (COD)Pt(SiMeCl$_2$)$_2$, where COD is 1,5-cyclooctadiene and Me is methyl. These alkene-platinum-silyl complexes may be prepared, for example by mixing 0.015 mole (COD)PtCl$_2$ with 0.045 mole COD and 0.0612 moles HMeSiCl$_2$.

The appropriate amount of the catalyst will depend upon the particular catalyst used. The platinum catalyst should be present in an amount sufficient to provide at least 2 parts per million (ppm), preferably 4 to 200 ppm of platinum based on total weight percent solids (all non-solvent ingredients) in the composition. It is highly preferred that the platinum is present in an amount sufficient to provide 4 to 150 weight ppm of platinum on the same basis. The catalyst may be added as a single species or as a mixture of two or more different species.

The hydrosilylation reaction between components a) and b) is conducted such that the molar ratio of the total alkenyl groups present in the hydrosilylation reaction to the SiH units (% H) in component a) is between 0.9/1 to 2.2/1.

The hydrosilylation reaction between components a) and b) may be conducted neat, or in the presence of a suitable solvent. Typically, the hydrosilylation reaction solvent is selected from one of the carrier fluids as described below as component B).

B) The Carrier Fluid

The organopolysiloxanes as described above are dispersed in a carrier fluid. Suitable carrier fluids include silicones, both linear and cyclic, organic oils, organic solvents and mixtures of these. Specific examples of solvents may be found in U.S. Pat. No. 6,200,581, which is hereby incorporated by reference for this purpose.

Typically, the carrier fluid is a low viscosity silicone or a volatile methyl siloxane or a volatile ethyl siloxane or a volatile methyl ethyl siloxane having a viscosity at 25° C. in the range of 1 to 1,000 mm$^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes.

Organic solvents may be exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons including isododecane, isohexadecane, Isopar L (C11-C13), Isopar H (C11-C12), hydrogentated polydecene. Ethers and esters including isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The amount of carrier fluid is such that there is 50 to 99.9 weight percent, alternatively 80 to 99.9 weight percent, alternatively 90 to 99.9 weight percent, of carrier fluid in the fluid composition.

The present fluid compositions may be prepared by simply combining components A) and B) and mixing. Typically however, it is more convenient to conduct the hydrosilylation reaction between components a) and b) to form component A) in the selected carrier fluid (component B)).

The pituitous silicone fluids compositions, or emulsions thereof, may be formulated into personal care products. The personal care compositions may be in the form of a cream, a gel, a powder, a paste, or a freely pourable liquid. Generally, such compositions can generally be prepared at room temperature if no solid materials at room temperature are presents in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

The present compositions can be used in a variety of personal, household, and healthcare applications. In particular, the compositions of the present invention may be used in the personal care products as taught in U.S. Pat. Nos. 6,051,216, 5,919,441, 5,981,680; as disclosed in WO 2004/060271 and WO 2004/060101; in sunscreen compositions as taught in WO 2004/060276; in cosmetic compositions also containing film-forming resins, as disclosed in WO 03/105801; in the cosmetic compositions as taught in US Patent Application Publications 2003/0235553, 2003/0072730, 2003/0170188, EP 1,266,647, EP 1,266,648, EP1,266,653, WO 03/105789, WO 2004/000247 and WO 03/106614; as additional agents to those taught in WO 2004/054523; in long wearing cosmetic compositions as taught in US Patent Application Publication 2004/0180032; in transparent or translucent care and/or make up compositions as discussed in WO 2004/054524; all of which are incorporated herein by reference.

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

Example 1

A series of pituitous silicone fluids were prepared by reacting vinyl-terminated dimethyl siloxane polymers with methylhydrogen cyclic siloxanes to produce highly branched fluids. In these examples, the stoichiometry of the reaction was controlled so as to produce a highly branched network but yet still below the gel point (the point where the number interconnections between siloxane chains are numerous enough to produce an elastomeric solid). The reaction vessel was charged with the dimethylvinyl-terminated dimethylsiloxane polymer (A) with an average degree of polymerization of ~4800 and a % vinyl level of ~150 ppm ($C_2H_3$) dispersed in Isopar™ L diluent. To this was added the tetramethylcyclotetrasiloxane (B) followed by platinum catalyst (C) diluted in dimethylvinyl-terminated dimethylsiloxane with a % vinyl level of 2.2% ($C_2H_3$). The reaction mixture was then heated to 85° C. for 18 hours resulting in a significant viscosity increase. The reaction mixture was then allowed to cool and poured from the reaction vessel. The table below summarizes the reactants and amounts used for examples 1 A, B, C, D, and E.

| Patent Example # | grams of A | grams of Diluent | milligrams of B | Wt. Ratio g of A/ mg of B | grams of C | Product Viscosity (cP)[a] |
|---|---|---|---|---|---|---|
| 1A | 2.00 | 38.17 | 1.39 | 1.44 | 0.015 | 64 |
| 1B | 2.00 | 38.17 | 1.50 | 1.33 | 0.015 | 200 |
| 1C | 2.00 | 38.17 | 1.61 | 1.25 | 0.015 | 460 |
| 1D | 25.00 | 477.12 | 20.21 | 1.24 | 0.19 | 1200 |
| 1E | 2.00 | 38.17 | 1.67 | 1.20 | 0.015 | 10000 |

[a]Measured on Brookfield model RVDV-II+ viscometer, LV spindle # 2 at 20 rpm.

FIG. 1 displays a plot of the Normal Stress (Pa) vs Shear Rate (1/sec) for the silicone fluid compositions of this Example using the controlled stress rheometer, as detailed above.

Example 2

A reaction vessel was charged with the dimethylvinyl-terminated dimethylsiloxane polymer with an average degree of polymerization of ~160 (A) dispersed in toluene diluent. To this was added the tetramethylcyclotetrasiloxane (B) and the platinum catalyst. The reaction mixture was then heated to 100° C. for 3.5 hours resulting in a significant viscosity increase. At this raw material ratio, the vinyl functionality is in excess resulting in the complete reaction of the SiH functionality. The reaction mixture was then allowed to cool and poured from the reaction vessel. The table below summarizes the reactants and amounts used for this example.

| Patent Example # | grams of A | grams of Diluent | grams of B | Vi:SiH Molar Ratio | grams of C | Product Viscosity (cP)[a] |
|---|---|---|---|---|---|---|
| 2A | 50.00 | 117.3 | 0.260 | 2.02 | 0.161 | 190 |
| 2B | 50.00 | 117.3 | 0.265 | 1.98 | 0.161 | 306 |
| 2C | 50.00 | 117.3 | 0.268 | 1.96 | 0.161 | 500 |

[a]Measured on Brookfield model RVDV-II+ viscometer, spindle # 6 at 100 rpm.

FIG. 2 displays a plot of the Normal Stress (Pa) vs Shear Rate (1/sec) for the silicone fluid compositions of this Example using the controlled stress rheometer, as detailed above.

The invention claimed is:
1. A fluid composition comprising:
A) 0.1 to 10 wt % of a branched organopolysiloxane prepared by reacting;
  a) an organohydrogencyclosiloxane having the formula [$(CH_3)HSiO]_g$ where g is 3 to 8, and,
  b) an alkenyl terminated polydiorganosiloxane comprising siloxy units of the formula $(R_2R^2SiO_{1/2})_v$ $(R_2SiO_{2/2})_x$
    where v≥2, and x≥50,
  R is an alkyl group containing 1 to 6 carbon atoms,
  $R^2$ is an alkenyl group containing 2 to 12 carbon atoms,
  in the presence of a hydrosilylation catalyst, where the molar ratio of alkenyl groups to SiH in the reaction is between 0.9/1 to 2.2/1, and
B) 90 to 99.9 wt % of a carrier fluid
selected from isododecane, isohexadecane, or isoparaffin, wherein the fluid composition has a viscosity of at least 300 mPa·s at 23° C. and exhibits pituitous rheological properties.
2. The fluid composition of claim 1 wherein the rheological properties of the fluid are determined from a plot of normal force in Pascals vs a perpendicular shear rate in sec$^{-1}$ wherein the plot has an average slope that is greater than 3.6.
3. The fluid composition of claim 2 where the alkenyl terminated polydiorganosiloxane is a vinyl terminated polydimethylsiloxane.
4. The fluid composition of claim 3 wherein the vinyl terminated polydimethylsiloxane is a gum.
5. The fluid composition of claim 1 where g is 4.

* * * * *